United States Patent [19]
Kasila et al.

[11] Patent Number: 5,972,595
[45] Date of Patent: Oct. 26, 1999

[54] ENZYME ASSAY USING A SOLID PHASE SUBSTRATE

[75] Inventors: Patricia Kasila, Windham, N.H.; Thomas R. Mullinax, Newton, Mass.; Michael E. Bembenek, Burlington, Mass.; Mark N. Bobrow, Lexington, Mass.

[73] Assignee: NEN Life Science Products, Inc., Boston, Mass.

[21] Appl. No.: 09/212,211

[22] Filed: Dec. 16, 1998

Related U.S. Application Data

[60] Provisional application No. 60/068,244, Dec. 19, 1997.

[51] Int. Cl.$^6$ .............. C12Q 1/00; C12Q 1/44; C12Q 1/34; C12Q 1/48
[52] U.S. Cl. .............. 435/4; 435/19; 435/18; 435/15
[58] Field of Search .............. 435/4, 19, 18, 435/15

[56] References Cited

U.S. PATENT DOCUMENTS

| | | | |
|---|---|---|---|
| 3,654,090 | 4/1972 | Schuurs et al. | 195/103.5 |
| 4,446,232 | 5/1984 | Liotta | 435/7 |
| 4,530,900 | 7/1985 | Marshall | 435/7 |
| 4,629,688 | 12/1986 | Bolguslaski et al. | 435/7 |
| 4,668,623 | 5/1987 | Kinnunen et al. | 435/19 |
| 4,937,188 | 6/1990 | Giese et al. | 435/41 |
| 5,104,815 | 4/1992 | Garner et al. | 436/505 |
| 5,190,864 | 3/1993 | Giese et al. | 435/41 |
| 5,238,817 | 8/1993 | Bobrow et al. | 435/28 |
| 5,304,465 | 4/1994 | Garland et al. | 435/4 |
| 5,328,831 | 7/1994 | Stewart et al. | 435/12 |

OTHER PUBLICATIONS

Camps et al. (1992) Stimulation of phospholipase C by guanine–nucleotide–binding protein By subunits. Eur. J. Biochem., 206:821–831.

Camps et al. (1990) Guanosine 5'–ly–thio triphosphate–stimulated hydrolysis of phosphatidylinositol 4,5–bisphosphate in HL–60 granulocytes. Biochem, J., 271:743–748.

Crooke and Bennett (1989) Mammalian phosphoinositide–specific phospholipase C isoenzymes. Cell Calcium, 10:309–323.

De Vivo (1994) Assays for G–protein regulation of phospholipase C activity. Methods in Enzymology, 238:131–141.

Gierschik et al. (1989) Dual Mg2+ control of formyl–peptide–receptor–G–protein interaction in HL 60 cells Evidence that the low–agonist–affinity receptor interacts with and activates the G–protein. Eur. J. Biochem., 183:97–105.

(List continued on next page.)

*Primary Examiner*—Louise N. Leary
*Attorney, Agent, or Firm*—Gifford, Krass, Groh, Sprinkle, Anderson & Citkowski, P.C.

[57] ABSTRACT

This invention relates to a hydrophobic layer formed on a solid support, the hydrophobic layer incorporating by hydrophobic interactions an amphipathic enzyme substrate labeled with a reporter on its hydrophilic region, and the use of the same to conduct various enzyme assays without extraction steps.

18 Claims, 4 Drawing Sheets

OTHER PUBLICATIONS

Haber et al. (1991) Activation of phosphoinositide–specific phospholipase Cδ from rat liver by polyamines and basic proteins. Arch. Biochem. Biophys., 288(1):243–249.

Hianik et al. (1996) Immobilization of enzymes on lipid bilayers on a metal support allows study of the biophysical mechanisms of enzymatic reactions. Bioelectrochemistry and Bioenergetics, 41:221–225.

Hoekstra and Duzgunes (1993) Lipid mixing assays to determine fusion in liposome systems. Methods in Enzymology, 220:15–32.

Miller and Racker (1976) Fusion of phospholipid vesicles reconstituted with cytochrome c oxidase and mitochondrial hydrophobic protein. J. Membr. Biol., 26:319–333.

Mueller et al. (1962) Reconstitution of excitable cell membrane structure in vitro. Circulation, 26:1167–1177.

Ottova and Tien (1997) Self–assembled bilayer lipid membranes: from mimicking biomembranes to practical applications. Bioelectrochemistry and Bioenergetics, 42:141–152.

Rhee and Choi (1992) Regulation of inositol phospholipid–specific phospholipase C isozymes. J. Biol. Chem., 267(18):12393–6.

Wright and Huang (1992) Bilayer stabilization of phosphatidylethanolamine by N–biotinylphosphatidylethanolamine. Biochim. Biophys. Acta, 1103:172–178.

Huang et al; Mol. Pharmacol; vol. 18(2), pp. 267–273;(1980).

PLC δ 1 Activity in the Presence and Absence of Additives
on [³H] PIP₂ Coated Phospholipid Support Plate

FIG - 2B

PLC δ 1 Activity in the Presence and Absence of Additives
on [³H] PIP₂ Coated Phospholipid Support Plate

ENZYME ASSAY USING A SOLID PHASE SUBSTRATE

This application claims the benefit of U.S. Provisional Application No. 60/068,244 filed Dec. 19, 1997.

FIELD OF THE INVENTION

This invention relates to a hydrophobic layer, such as a lipid layer formed on a solid support, the lipid layer incorporating by hydrophobic interactions an amphipathic enzyme substrate labeled with a reporter on its hydrophilc region, and the use of the same to conduct various enzyme assays without extraction steps.

BACKGROUND OF THE INVENTION

Because many intracellular and intercellular processes are membrane mediated, there has been a great deal of research on the reconstitution of biological membranes as a method to study these processes. Since the original development of a procedure to form artificial planar phospholipid bilayer membranes (Mueller et al., 1962) and the demonstration of the fusion of vesicles that contain ion channels to planar membranes (Miller and Racker, 1976), studies have employed a variety of artificial membrane systems and various methods for studying functional molecules that are incorporated in or bound to biological membranes (Hoekstra and Duzgunes, 1993). Some researchers have incorporated biotinylated lipids (e.g., see Wright and Huang, 1992) or functional enzymes (e.g., see Hianik et al., 1996) into artificial membranes, but the purpose has been to study properties of the membranes or the incorporated molecules, not to use the synthetic membranes as a tool to study the properties of exogenous molecules as in the present invention. For a review of current techniques and research in this area (see Ottova and Tien, 1997).

Phospholipase C (PLC) is a generic name for enzymes that catalyze the hydrolysis of phosphoglycerides into diacylglycerols and phosphorylated alcohols such as serine, choline, inositol, glycerol, or ethanolamine. For example, a specific phospholipase C hydrolyzes phosphatidylinositol-4-phosphate (PIP) or phosphatidylinositol-4,5-bisphosphate ($PIP_2$), resulting in each case in the formation of two second messengers: a hydrophobic diacylglycerol and a hydrophilic inositol phosphate ($IP_2$ or $IP_3$ respectively). This hydrolysis can be monitored by a variety of methods using endogenously or exogenously labeled substrates.

De Vivo (1994) describes current methods used for measuring the hydrolysis of $PIP_2$. In the endogenous substrate approach, the cells of interest are cultured in the presence-[$^3$H]-inositol. The cells convert inositol to phosphatidylinositol (PI) using phosphatidylinositol synthase, and the PI in turn is converted to PIP-[$^3$H] and $PIP_2$-[$^3$H] by phosphatidylinositol kinases. When the polyphosphoinositide pool is labeled to a steady state, the breakdown of PIP and $PIP_2$ is initiated by the addition to the cell culture medium of an appropriate stimulatory factor (e.g., receptor agonists for intact cells or guanylyl nucleotides for permeabilized cells).

In the exogenous substrate approach, purified labeled phospholipids are used as the substrate. The phospholipids are mixed in the presence or absence of detergent and sonicated briefly on ice to prepare vesicles. Aliquots of the substrate are mixed with a source of PLC (membranes or purified enzyme) and, often, G-protein subunits.

In both the endogenous and exogenous substrate approaches, solvent extraction is used to separate the hydrophilic reaction products from the hydrophobic substrate. Current methods for sphingomyelinase assays also require solvent extraction steps. It would be desirable to eliminate the extraction step for environmental and health reasons. In addition, it is difficult to automate the extraction of large numbers of samples, as would be necessary for example in high throughput screening of drug candidates.

SUMMARY OF THE INVENTION

The invention described here allows the quantitative or qualitative determination of the enzymatic activity of various enzymes without requiring an extraction step. As a substrate, the invention uses a solid support coated with a hydrophobic layer, such as an artificial lipid layer, incorporating by hydrophobic interactions an amphipathic enzyme substrate labeled so that a labeled hydrophilic fragment will be produced when the substrate is cleaved by a specific enzyme. The labeled hydrophilic fragment will migrate into the aqueous phase, thereby no longer being associated with the solid support, forming the basis for an assay of the activity of the enzyme. Selection of an appropriate labeled substrate allows the use of the invention with a variety of enzymes.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

The unique feature of this invention is the use of a substrate that allows the study of enzyme activity in samples without the need to extract the reaction products. The invention can be used in either homogeneous or heterogeneous assay formats and can employ either radiometric or non-radiometric substrates. With appropriate substrate design, the present invention can be used to study a variety of enzymes, such as phospholipases, for which the assay methods otherwise require extraction steps. Substrates suitable for use in the invention include, but are not limited to phospholipids, sphingolipids, and any other amphipathic molecules, such as glycosyldiacylglycerols, ceramides, gangliosides, and complex phospholipids like cardiolipin. The enzyme used can be purified, semi-purified or a crude extract.

An amphipathic enzyme substrate labeled on a polar moiety is incorporated by hydrophobic interactions into any suitable hydrophobic layer, such as a lipid layer, that is formed on a solid support and is retained by hydrophobic interaction and/or by covalent attachment. A suitable hydrophobic layer is one that incorporates a component that binds the amphipathic substrate by hydrophobic interaction. The particular substrate to use is designed or selected for its susceptibility to the action of the enzyme of interest and an appropriate location for the label. Suitable reporter group(s) used to label the substrate include, but are not limited to radioactive isotopes, enzymes, fluorogenic, calorimetric, magnetic, chemiluminescent or electrochemical materials or a member of a specific binding pair.

Suitable solid phase supports include but are not limited to synthetic polymer supports such as polystyrene, polypropylene, substituted polystyrene, e.g., laminated or carboxylated polystyrene; polyacrylamides; polyamides; polyvinylchloride, etc.; glass beads; agarose; nitrocellulose; nylon; polyvinylidenedifluoride; surface-modified nylon, etc. Homogeneous assay methods for phospholipases employing a 96-well FlashPlate as the solid support have been shown to work well. (A FlashPlate is a 96-well white polystyrene microplate in which the interior of each well is coated with a thin layer of polystyrene-based scintillant.)

It will thus be seen that the present invention is directed to a method and material for carrying out rapid, enzyme based assays. The assays may be quantitative or qualitative, and do not require extensive sample preparation or extraction steps. The assays rely upon the use of an amphipathic substrate which is reactive with the enzyme. The amphipathic substrate includes a hydrophilic portion which carries a reporter moiety (also referred to as a label), and a hydrophobic portion.

In a typical assay, a sample of material, including the suspected target enzyme, is placed in contact with the hydrophobic layer, which as previously noted is preferably disposed upon a support. The sample is disposed in a polar solvent which typically comprises water, and at least a portion of the enzyme which is in the sample will interact with the substrate material therein. This interaction results in a cleavage of the substrate, which releases a hydrophilic fragment including the reporter material thereupon. The hydrophilic fragment has a low affinity for the hydrophobic layer, and migrates into the exterior, polar solvent. Detection of the reaction is most preferably accomplished by measuring the residual reporter activity of the hydrophobic layer, and this residual reporter activity will be inversely proportional to the activity of the enzyme in the sample. Alternatively, enzyme activity may be measured by detecting the reporter label fragments in the aqueous material.

As noted hereinabove, the reporter moiety may comprise a radioactive species such as tritium, and in some instances, the hydrophobic layer may be disposed upon a support which includes a scintillator material therein. In other instances, the reporter material may comprise a magnetically labeled material, a fluorescent labeled material, a member of an antibody/antigen pair, a fluorescent agent, a color forming agent, a chemiluminescent material, an enzyme different from the target enzyme of the assay, an electrochemically active material, or the like, and other such reporter materials will be apparent to one of skill in the art.

The following examples are intended to illustrate the invention.

EXAMPLE I

Sphingomyelinase Assay

Preparation of Substrate—FlashPlates coated with streptavidin were obtained from NEN Life Science Products™. Biotinylated phosphatidylethanolamine (PE) (Avanti) was diluted to 10 micrograms/mL in PBS (0.1 M NaCl in 0.01 M sodium phosphate buffer, pH 7.4) and 0.1 mL was added to each well. After incubation overnight at room temperature to allow binding to the streptavidin, the remaining solution was removed from the wells by aspiration. Sphingomyelin (egg), [choline methyl-$^3$H] (NEN Life Science Products, Inc.) was diluted to 1.0 microcurie/mL with Tris-HCl, pH 7.0 containing 0.1% bovine serum albumin [BSA] and 0.1 mL was added to each well. During overnight incubation at room temperature, the sphingomyelin hydrophobically interacted with the PE to form a $^3$H-labeled solid-phase lipid layer. Plates were then aspirated and air-dried.

Enzyme Assay—Sphingomyelinase (Sigma) was serially diluted in PBS containing 1 mg/mL $CaCl_2$ and 1 mg/mL $MgCl_2$ (BioWhittaker) and 0.1 mL was added to each well and incubated overnight at room temperature. The hydrophilic $^3$H-labeled fragment cleaved from the sphingomyelin by the activity of sphingomyelinase moved from the hydrophobic solid-phase lipid layer into the aqueous solution, decreasing the amount of $^3$H within sufficient proximity of the scintillant to be counted. The results in Table 1 show that increasing the amount of sphingomyelinase produced a decrease in the amount of radioactivity detected in the well. The well with no sphingomyelinase was used as a negative control.

TABLE 1

| Sphingomyelinase (mU/mL) | Counts per Minute (CPM) | Percent of Negative Control |
|---|---|---|
| 2000 | 1038 | 8.6 |
| 200 | 2144 | 17.7 |
| 20 | 4672 | 38.6 |
| 2 | 8933 | 73.8 |
| 0.2 | 10691 | 88.4 |
| 0 | 12099 | 100.0 |

EXAMPLE II

Phospholipase C Assay

Preparation of Substrate—FlashPlates were prepared exactly as in Example 1 except that $PIP_2$ [inositol-2-$^3$H(N)]

(NEN Life Science Products) was added instead of sphingomyelin-[$^3$H] in the preparation of a $^3$H-labeled solid-phase lipid layer.

Partial Purification of PLC—(Camps et al. 1992; Camps et al. 1990; Glorschik et al. 1989). For maintenance, HL-60 cells (ATCC CCL-240) were cultured in 1-liter spinner flasks at 10% $CO_2$ in Iscove's Medium supplemented with 20% fetal bovine serum (FBS), 1% L-glutamine and 0.1% gentamicin. To induce phospholipase C, the cells were cultured in media supplemented with 1.25% dimethylsulfoxide (DMSO) for five days, or until a density of about $2$–$3 \times 10^6$ viable cells was reached. After harvesting by centrifugation and washing twice with wash buffer (20 mM Tris-HCl (pH 7.5), 1 mM EDTA, 1 mM dithiothreitol, 3 mM benzamidine, 1 mM leupeptin, 1 mM phenylmethyl sulfonyl fluoride (PMSF) and 0.002 mM soybean trypsin inhibitor), the final pellet containing about $2 \times 10^{10}$ cells (30 mL packed cell volume) was resuspended in 50–100 mL of Lysis Buffer (250 mM sucrose, 20 mM Tris-HCl [pH 7.5], 1.5 mM $MgCl_2$, 1 mM ATP, 3 mM benzamidine, 0.001 mM leupeptin, 1 mM PMSF, 0.002 mM soybean trypsin inhibitor). The cells were lysed by four treatments in the cold for one minute each with a Polytron homogenizer with a one minute rest between treatments, followed by sonication in an ice bath four times for one minute with a one minute rest between treatments. The lysate was supplemented with EGTA to 1.25 mM, and debris was removed by a 4° C. centrifugation at 1445×g for twenty minutes. The resulting supernatant was centrifuged at 4° C. for twenty minutes at 17,593×g. The supernatant from this step was centrifuged at 4° C. for sixty minutes at 112,594×g. The final supernatant (cytosol) was passed through a 0.45 micrometer pore size filter. After determination of the protein concentration, the cytosol was snap frozen and stored at −80° C., until used as a source of phospholipase C.

Enzyme Assay—To assay phospholipase C activity, the thawed HL-60 cytosol was diluted to various protein concentrations with PBS containing 0.4 mM $CaCl_2$ and 0.21 mM GTP-gamma-S. Diluted cytosol (0.1 mL) was added to each FlashPlate® well containing a solid-phase lipid layer with $PIP_2$-[$^3$H], and incubated overnight at room temperature. The hydrophilic $^3$H-labeled fragment cleaved from the $PIP_2$ by the activity of phospholipase C moved from the hydrophobic solid-phase lipid layer into the aqueous solution, decreasing the amount of $^3$H label within sufficient proximity of the scintillant to be counted. The results in Table 2 show that increasing the amount of phospholipase C produced a decrease in the amount of radioactivity detected in the well. The well with no phospholipase C was used as a negative control.

TABLE 2

| Phospholipase C (mg/mL of HL-60 cytosol protein) | Counts per Minute (CPM) | Percent of Negative Control |
| --- | --- | --- |
| 3.5 | 864 | 31.1 |
| 1.0 | 1072 | 38.5 |
| 0 | 2782 | 100 |

EXAMPLE III

Chemical Surface Modification of FlashPlates for Covalent Linkage of Phosphatidylethanolamine Two types of chemistries are involved: one employing divinylsulfone (DVS) and the other using 1-3-(3-dimethylaminopropyl)carbodiimide(EDAC). Divinylsulfone Plate Activation: A 1% DVS solution is prepared in 0.1 M sodium carbonate, pH 11.5, immediately prior to use. Aliquots (0.2 Ml) are distributed to individual wells and the plate allowed to stand at room temperature for at least thirty minutes. The plate is then washed thrice with 0.1 M sodium carbonate, pH 10.5, and then air dried briefly prior to adding the lipid. A 25 μg/ml solution of phosphatidylethanolamine (PE) is made in 25–50 mM sodium carbonate, pH 9.8–10.2 and 0.2 ml distributed to each well. The plate is incubated again at room temperature for at least three hours. Finally, the plate is washed twice with phosphate buffered saline (PBS), 0.04% deoxycholate and twice with PBS alone. The plate is then air dried and stored in a sealed bag in the dark at room temperature. EDAC Plate Activation: A solution of 0.5 mg/ml EDAC is prepared in 10–50 mM MES, pH 6.8–7.2, containing 25 μg/ml of PE and 0.2 ml is distributed to individual wells. The plate is allowed to stand overnight at room temperature in the dark. Finally, the plate is washed twice with phosphate buffered saline (PBS), 0.04% deoxycholate and twice with PBS alone. The plate is then air dried and stored in a sealed bag in the dark at room temperature.

Introduction:

Inositol specific phospholipase Cs (PLCs) are key enzymes in the signal transduction of many cell mediated responses as diverse as peptide hormones and neurotransmitters (Rhee and Choi, 1992). These enzymes are specific hydrolases for the phosphoinositide. The enzyme reaction of the PLCs with phosphatidylinositol 4,5-bisphosphate ($PIP_2$) results in the production of inositol 1,4,5-trisphosphate ($IP_3$) and diacylglycerol. It is the generation of these products that produces the cascade of regulatory signals throughout the cell. $IP_3$ induces the intracellular release of $Ca^{2+}$ stores from the endoplasmic reticulum through its specific interactions with the $IP_3$ receptor, whereas, diacylglycerol is a potent activator of protein kinase C. The activation of these cellular events results in a stimulation of a series of pathways that modulate cellular activity.

Classically, PLC enzymes are divided into three families designed β, δ and γ. The β and γ are regulated either through the G-protein coupled pathway or the receptor mediated tyrosine kinase pathway, respectively. Activity of these enzymes has been historically studied using solution based assays with phospholipid vesicles containing trace amounts of [$^3$H, inositol] $PIP_2$ (DeVivo, 1994). The hydrolytic reaction is monitored by the addition of acidified organic solvents and subsequent phase separation. [$^3$H] $IP_3$ remains in the aqueous phase while the acidic labeled lipids partition into the organic layer. Thus, simple radioassays of the aqueous layer provide a convenient way to measure PLC activity. However, the limits of the assay are that it is not readily amenable to high-throughput screening (HTS) methods.

In order to study these enzymes in high throughput fashion, a method was developed for monitoring PLC activity on FlashPlates™ containing bound [$^3$H] phosphatidylinositol 4,5-bisphosphate. The FlashPlate™ was modified in order to capture labeled phospholipids onto the surface and, thereby, provide a functional substrate to gauge PLC activity.

Methods:

Phospholipid modified FlashPlate™ were made by a variety of different methods in order to test various coating surfaces. Ninety-six well Phospholipid FlashPlates™ were coated with 0.2 ml of a solution containing [1-$^3$H, inositol] $PIP_2$ (~20 Ci/mmol, NEN) at concentrations between 0.25–1 μCi/ml for at least three hours. The wells were then washed twice with phosphate buffered saline (PBS) containing 0.04% sodium deoxycholate and finally with PBS alone. Typically, coefficient of variation ranged between 8–12%. Reactions were conducted directly in the wells in buffer indicated in the legends and monitored on a Packard Top-Count™ instrument.

One unit of PLC activity is defined as one nmol of [$^3$H] IP$_3$ formed per minute per mg of enzyme using typical solution based assays (DeVivo, 1994).

HL60 cells were grown to late log phase prior to harvest and the cytosolic fraction prepared as previously described (Camps et al. (1990; Camps et al. 1992) or HL60 cytosolic extracts were purchased commercially from ABS, Inc. A431 human epidermoid carcinoma cells were grown in 150 cm$^2$ culture flasks containing Dulbecco's modified Eagle's medium (DMEM) with 10% fetal calf serum (FCS) prior to harvesting. A431 cells were cultured until ~50% confluency was reached. Cells were harvested by scraping the attached cell mass from the bottom of the flask and pelleting by low speed centrifugation. Cell pellets were then rinsed twice with PBS. Cells were resuspended in a minimal volume of reaction buffer containing 10 units/ml streptolysin S and counted prior to being aliquoted to individual wells.

All other chemicals or reagents were of reagent grade or better.

Figure 1:
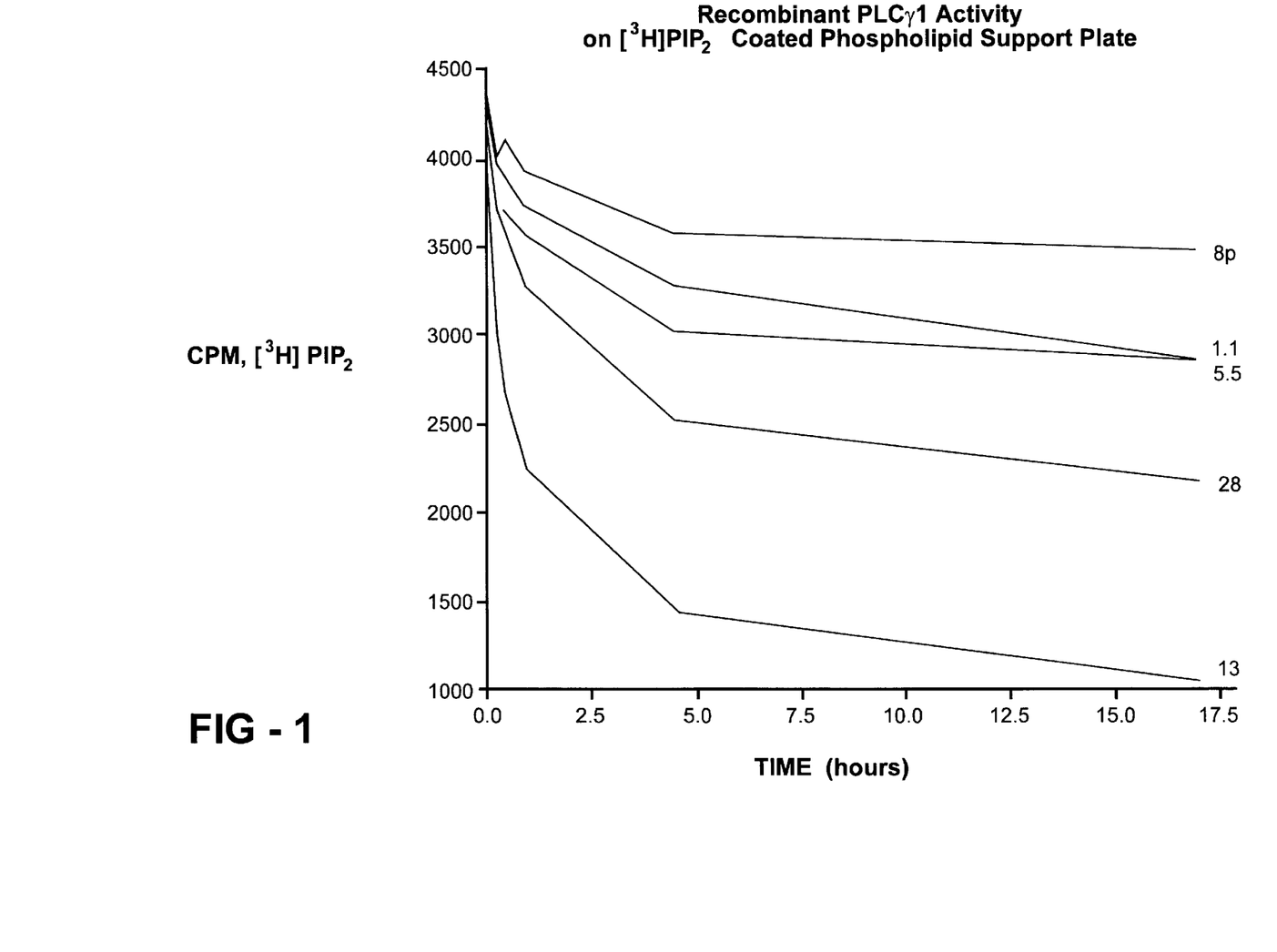
FIG. 1 is a graph illustrating kinetic activity of various amounts of purified recombinant PLC γ1 on [$^3$H] $PIP_2$ coated 96-well phospholipid FlashPlate™. Different concentrations of purified recombinant PLC were added to individual wells in 0.1 ml of 50 mM $NaP_i$, pH 6.7, 0.1 M NaCl, 0.1 mM $CaCl_2$, 0.1 mM EGTA and the release of radioactivity was monitored as a function of time on a Packard TopCount™. (Microplate Scan System manufactured by the Packard Instrument Company of Meriden, Conn.).

Results:

Our initial work served to verify that the labeled surface of the Phospholipid FlashPlate™ could effectively present the inositol headgroup to the enzyme for hydrolysis. Over the course of the 17.5 hour reaction purified recombinant PLC γ1 displayed an ability to release bound counts in a concentration dependent fashion (see FIG. 1). In all instances the reaction of PLC γ1 plateaued within the first five hours of the reaction and produced very little release of counts thereafter. At the highest concentration of enzyme tested, 130 μg, over 75% of the radioactivity was released from the plate surface. These results indicated that the majority of the surface bound [$^3$H] PIP$_2$ is readily available as a substrate for the enzyme. In order to verify that the release of surface bound counts was in fact due to hydrolysis of the [$^3$H] PIP$_2$ individual wells were aspirated and extracted with two volumes of chloroform-methanol under acidic conditions (CHCl$_3$: CH$_3$OH:HCl, 2:1:0.01). The relative distribution of radioactivity in the organic and aqueous phase represents labeled PIP$_2$ and IP$_3$, respectively. As shown in Table 3, release of radioactivity from the labeled Phospholipid FlashPlate™ was due predominantly to the hydrolysis of the bound [$^3$H] PIP$_2$ with both crude PLC preparations from HL60 cytosolic extracts and recombinant PLC (control wells showed little or no release of radioactivity, data not shown). In both instances, the radioactivity was distributed mostly into the aqueous phase (~90% and above) indicative of [$^3$H]IP$_3$. This result shows that labeled IP$_3$ was being specifically released from the Phospholipid FlashPlate™ and that surface bound labeled PIP$_2$ was in fact a viable substrate for both crude enzymatic PLC preparations of HL60 cytosolic extracts, as well as the purified recombinant PLC.

TABLE 3

Post-reaction Organic Extraction of Aqueous Samples from Individual Wells of [$^3$H] PIP$_2$ Coated Phospholipid FlashPlate ™

| | % Distribution | |
| --- | --- | --- |
| Sample (# of experiments) | Aqueous Phase ([$^3$H]IP$_3$) | Organic Phase ([$^3$H]PIP$_2$) |
| HL60 cytosol (n = 10) | 89 ± 7.5% | 11 ± 1.1% |
| Recombinant PLC (n = 3) | 97 ± 0.3% | 3 ± 0.15% |

Figure 2A:
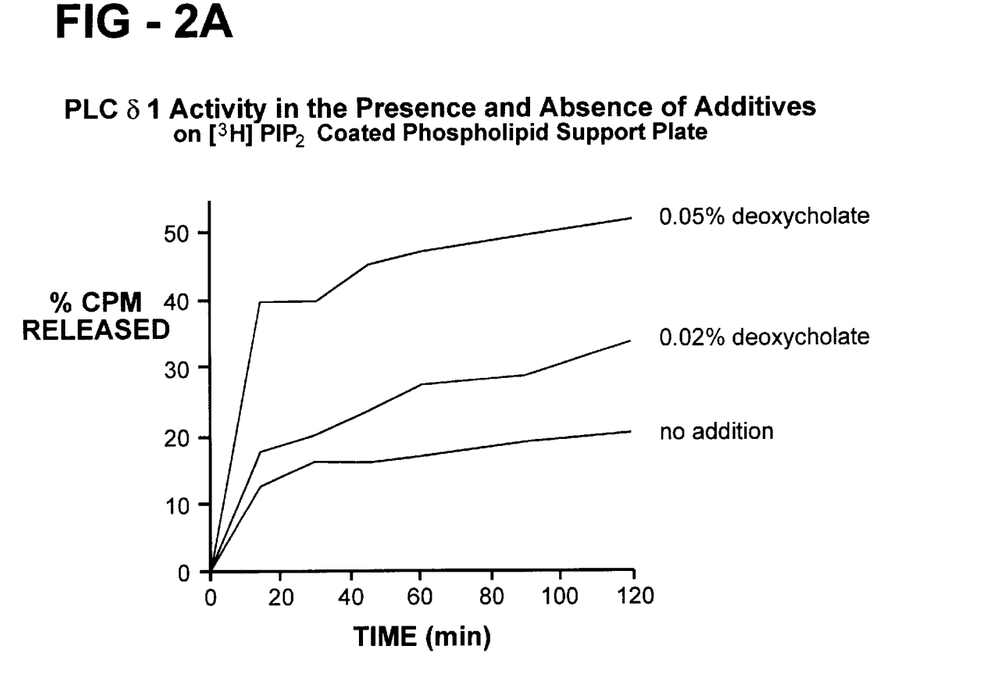
FIG. 2A is a graph illustrating the effects of additives to PLC δ1 activity against [$^3$H] $PIP_2$ coated 96-well phospholipid FlashPlate™ wherein the effects of different concentrations of deoxycholate on the release of radioactivity as a function of time by 13 mU PLC in 0.2 ml HEPES-NaOH, pH 7.0, 0.14 M KCl, 0.1 mM $CaCl_2$, 0.1 mM EGTA, [deoxycholate]'s on a % (wt/vol) basis.
Figure 2B:
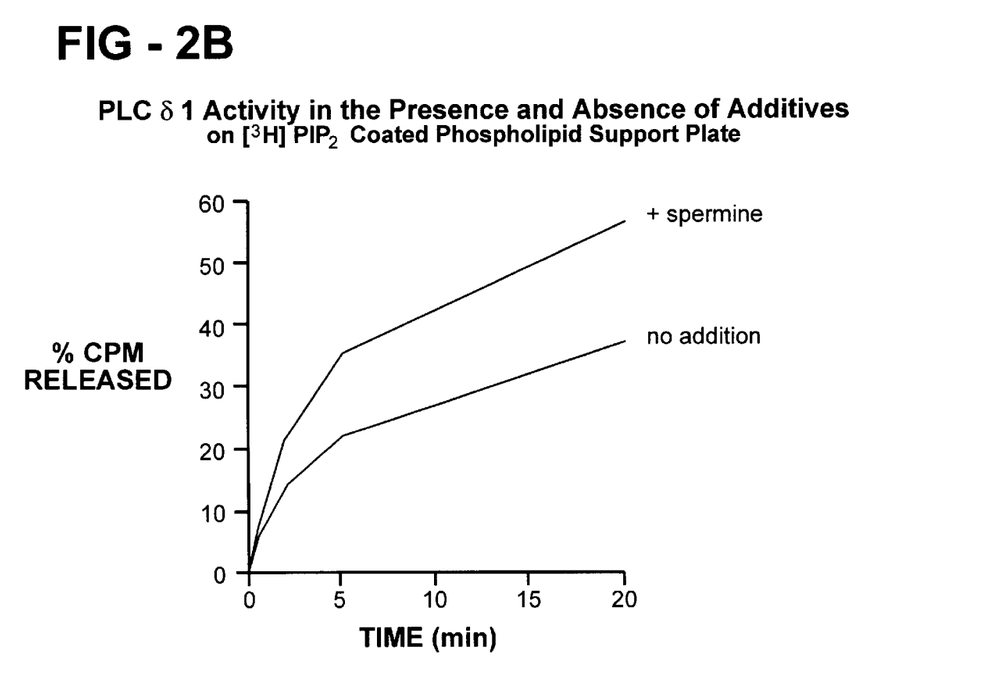
FIG. 2B is a graph illustrating the effect of the addition of 0.2 mM spermine on 100 mU PLC activity in 0.2 ml 50 mM HEPES-NaOH, pH 6.7, 0.15 M KCl, 0.1 mM $CaCl_2$, 0.1 mM EGTA, 0.04% deoxycholate (wt/vol). The release of radioactivity was monitored on a Packard TopCount™.

The reaction also displayed many of the same characteristics as had previously been shown for solution based assays using mixed micelles in the presence of either deoxycholate (Crooke and Bennett, 1989) or spermine (Haber et al., 1991). For these assays recombinant PLC δ1 showed enhanced hydrolytic activity in a concentration dependent manner upon addition of sodium deoxycholate (see FIG. 2A) or in the presence of added spermine (see FIG. 2B). The results confirm the effects of these compounds on the stimulation of PLC activity as had been previously published (Crooke and Bennett, 1989; Haber et al. 1989) and validate the utility of the plate format when compared to solution based micelle assays.

Figure 3:
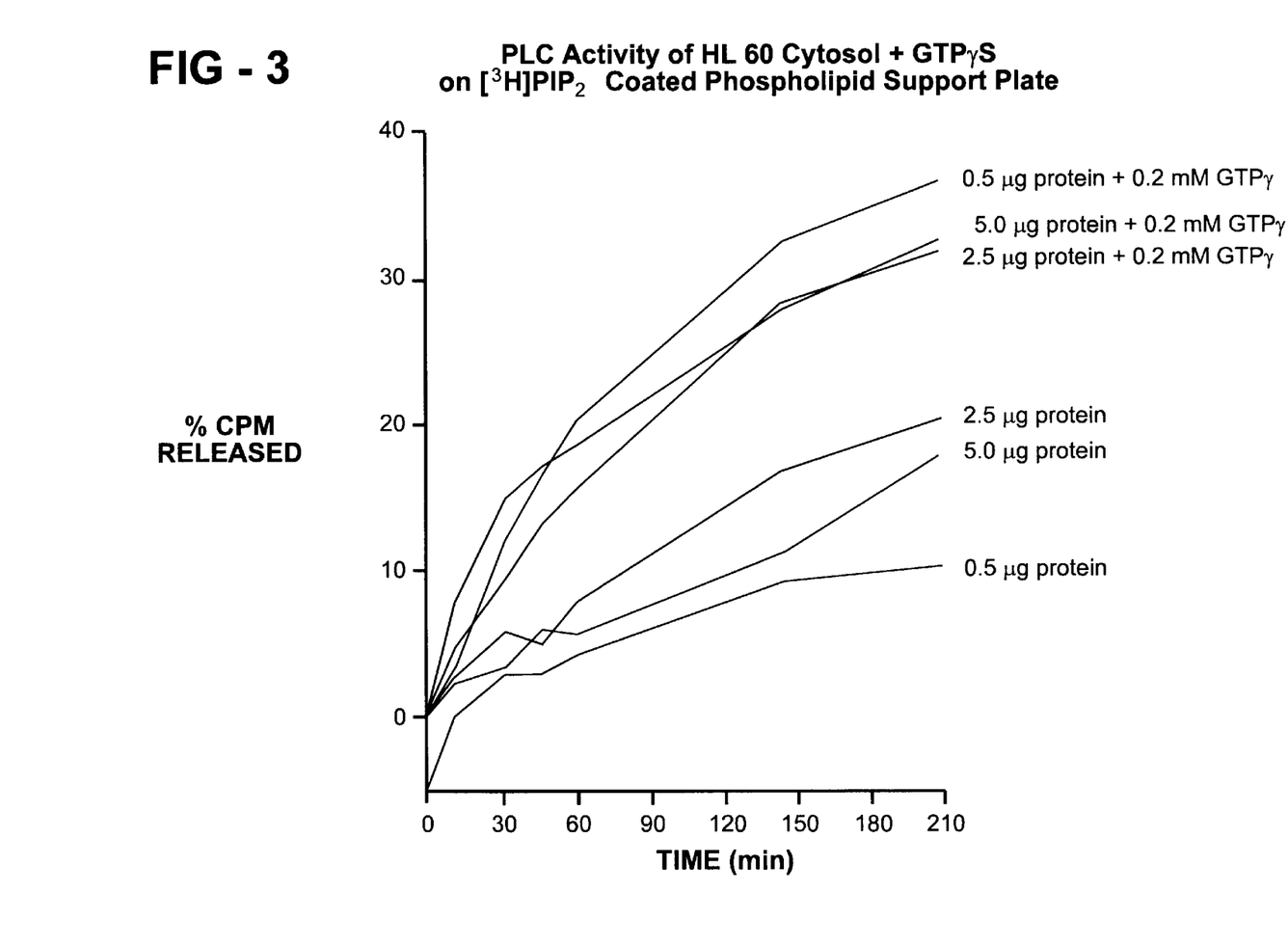
FIG. 3 is a graph illustrating the stimulation of PLC activity by addition of GTPγS to crude HL60 cytosolic preparations by GTPγS as measured on [3H] $PIP_2$ coated 96-well phospholipid FlashPlates™. Various amounts of HL60 cytosol protein were added to individual wells containing 0.2 ml 50 mM HEPES-NaOH, pH 6.7, 0.15 MKCl, 0.1 mM $CaCl_2$, 0.1 mM EGTA, 0.04% deoxycholate (wt/vol) either in the presence or absence of 0.2 mM GTPYS. The release of radioactivity was monitored on a Packard TopCount™.

Other experiments were designed to explore whether the stimulation of PLC activity from crude cellular extracts could be monitored on the Phospholipid FlashPlate™ using previously described protocols (Rhee and Choi, 1992; DeVivo 1994). Various protein concentrations of HL60 cytosolic extracts were treated in the presence or absence of the non-hydrolyzable analog GTPγS and the decrease of radioactivity was monitored kinetically. As shown in FIG. 3, in the absence of the analog the release of bound counts displayed a concentration dependence upon the amount of protein added and the reaction began to taper off by three hours at ~15%. Addition of GTPγS to the samples produced a stimulation in PLC activity at every protein concentration tested. However, the concentration dependence of added protein appeared to be lost possibly due to the fact that only low substrate levels were available on the surface. Even despite this, a clear 2–3 fold stimulation was evident for each protein concentration used.

Figure 4:
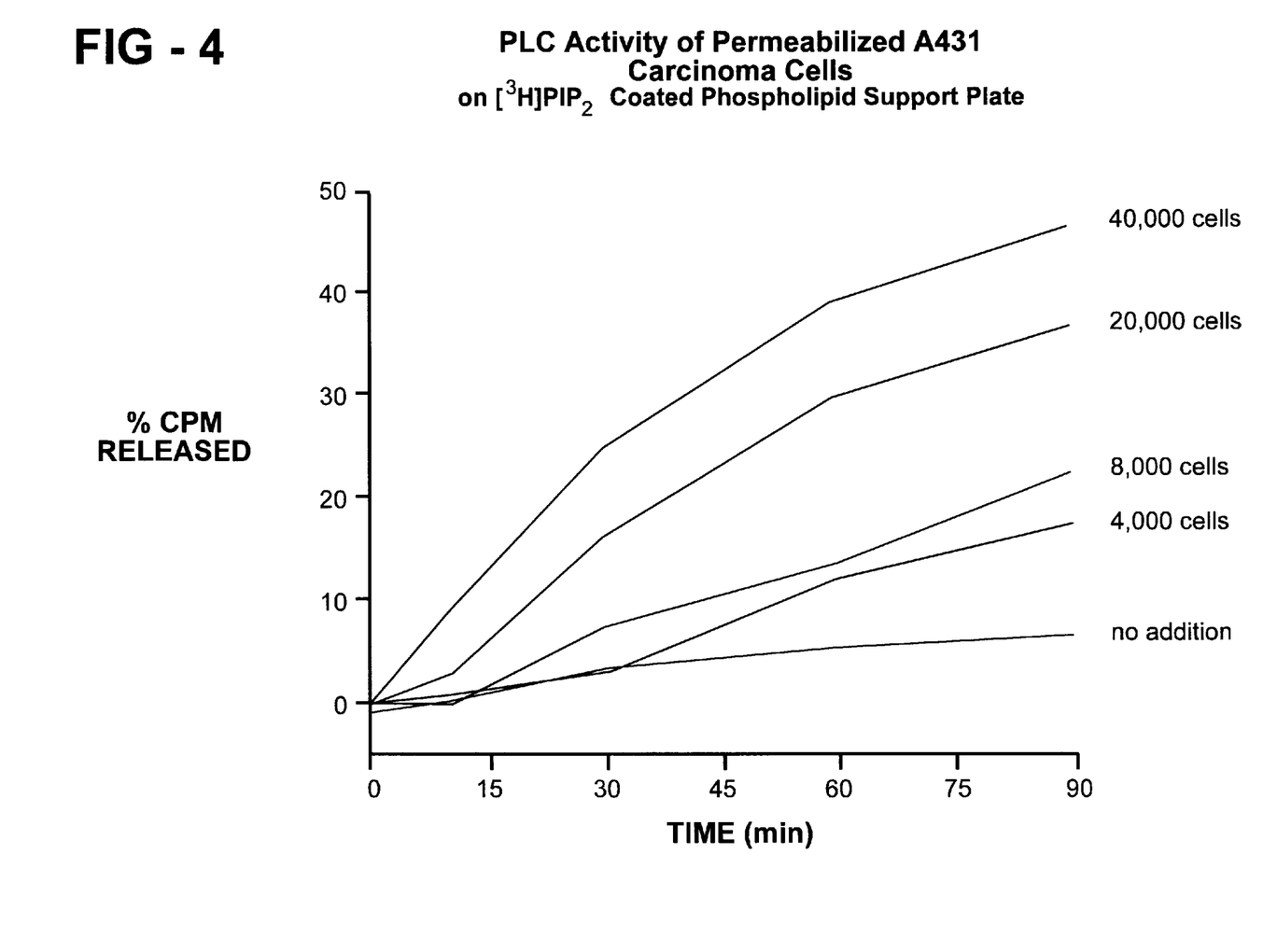
FIG. 4 is a graph illustrating the release of intracellular PLC activity from streptolysin S permeabilized A431 human carcinoma cells as measured on [3H] $PIP_2$ coated 96-well phospholipid FlashPlate™. Aliquots of resuspended A431 cells were distributed into wells containing 50 mM HEPES-NaOH, pH 6.7, 0.15 M KCl, 0.1 mM $CaCl_2$, 0.1 mM EGTA, 0.04% deoxycholate (wt/vol), 10 units/ml streptolysin S and the volume adjusted to 0.2 ml with reaction buffer. The release of radioactivity was monitored on a Packard Top-Count™.

As a further test of this format, we analyzed the activity of PLC as released from permeabilized A431 human epidermoid carcinoma cells (see FIG. 4). In this instance, addition of various amounts of cells to the [$^3$H] PIP$_2$ coated Phospholipid FlashPlate resulted in the release of radioactivity in a cell number dependent manner. Cell numbers at and below 2×10$^5$ cells/ml showed an initial lag phase on the reaction indicating a delay in the release of PLC activity from the cells. Moreover, at cell numbers about 2×10$^5$ cells/ml the release of radioactivity from the surface could be shown to be due to the release of both intact lipid and IP$_3$ (data not shown). Therefore, at elevated cell numbers this result suggests that other cellular components are capable of removing the lipid from the surface in a non-hydrolytic reaction. Cumulatively these results demonstrate that PLC activity can be monitored from both permeabilized cells and cytosolic extracts in a high throughput fashion on [$^3$H]PIP$_2$ Coated Phospholipid FlashPlates™.

Conclusions:

This work clearly demonstrates the utility of [$^3$H] PIP$_2$ coated phospholipid FlashPlates™ for monitoring PLC activity for high throughput screening of receptor-coupled functional assays. The results indicate that PLC activity can be monitored easily from a variety of sources including purified recombinant enzyme preparations to crude cell lysates and permeabilized cells. Moreover, this format provides a surface comparable to that used for classical labeled micelle studies and illustrates the feasibility of this assay for measuring PLC activity in a variety of different drug screening assays.

The principles of the present invention may be adapted to a variety of enzyme/substrate systems all of which will be apparent to one of skill in the art. In view of the foregoing, it will be understood and appreciated that numerous modifications and variations of the aforedescribed invention may be readily implemented. The discussion, description and examples set forth herein are illustrative of particular embodiments of the present invention, but are not meant to be limitations upon the practice thereof It is the following claims, including all equivalents, which define the scope of the invention.

LITERATURE CITED

Camps et al. (1992) *Eur. J. Biochem.* 206:821–831.
Camps et al. (1990) *Biochem. J.* 271:743–748.
Crooke and Bennett (1989) *Cell Calcium,* 10:309–23.
De Vivo (1994) Assays for G-protein regulation of phospholipase C activity. *Methods in Enzymology* 238: 131–141.
Gierschik et al. (1989) *Eur. J. Biochem.* 183:97–105.
Haber et al. (1991) *Arch. Biochem. Biophys.,* 288(1):243–6.
Hianik et al (1996) Immobilization of enzymes on lipid bilayers on a metal support allows study of the biophysical mechanisms of enzymatic reactions. *Bioelectrochemistry and Bioenergetics* 41:221–225.
Hoekstra and Duzgunes (1993) Lipid mixing assays to determine fusion in liposome systems. *Meth. Enz.* 220:15–32.
Miller and Racker (1976) *J. Membr. Biol.* 26:319.
Mueller et al. (1962) *Circulation* 26:1167.
Ottova and Tien (1997) Self-assembled bilayer lipid membranes: from mimicking biomembranes to practical applications. *Bioelectrochemistry and Bioenergetics* 42: 141–152.
Rhee and Choi (1992)*J. Biol. Chem.,* 267(18):12393–6.
Wright and Huang (1992) Bilayer stabilization of phosphatidylethanolamine by N-biotinylphosphatidylethanolamine. *Biochim. Biophys. Acta* 1103:172–178.

We claim:

1. A method for analyzing a sample for the presence and/or activity of an enzyme, said method comprising the steps of:
    providing a hydrophobic material;
    providing an amphipathic substrate having a hydrophobic portion, and a hydrophilic portion, said hydrophilic portion including a reporter moiety thereupon, said substrate being capable of being cleaved by said enzyme so as to produce a hydrophilic fragment which includes said reporter moiety;
    disposing said substrate in said hydrophobic material;
    contacting the hydrophobic material having said substrate disposed therein, with said sample and with a polar solvent, whereby any of said enzyme which is present in said sample will cleave said substrate and produce said labeled hydrophilic fragment, which fragment will migrate into said polar solvent; and
    detecting the presence of said reporter in said polar solvent or in said hydrophobic layer; whereby the presence of said reporter in said polar solvent and/or the reduction of the quantity of said reporter in said hydrophobic layer is indicative of activity of said enzyme.

2. The method as in claim 1, wherein said hydrophobic material comprises a layer.

3. The method as in claim 2, wherein the step of detecting the presence of said reporter comprises detecting the amount of said reporter in said hydrophobic layer; wherein the concentration of said reporter in said hydrophobic layer is inversely proportional to the activity of said enzyme.

4. The method as in claim 1, wherein the step of detecting the presence of said reporter comprises detecting the amount of said reporter in said polar solvent; whereby the concentration of said reporter in said polar solvent is proportional to the activity of the enzyme.

5. The method as in claim 1, wherein the step of providing a hydrophobic material comprises the further step of supporting said hydrophobic material on a support.

6. The method as in claim 5, wherein said support comprises a micro-well plate.

7. The method as in claim 5, wherein said support comprises a plurality of beads.

8. The method as in claim 5, wherein said reporter is a radioactive material and wherein said support includes a radiation responsive material.

9. The method as in claim 5, wherein said reporter is a non-radioactive material and wherein said support includes a responsive material.

10. The method as in claim 2, wherein said hydrophobic layer is covalently attached to said support.

11. The method as in claim 2, wherein said hydrophobic layer is a lipid.

12. The method as in claim 11, wherein said lipid comprises phosphatidylethanolamine.

13. An assay for analyzing a sample for the presence of an enzyme therein, said assay comprising:
    a body of a hydrophobic material;
    an amphipathic substrate disposed in said hydrophobic material, said amphipathic substrate including a hydrophobic portion which interacts with said hydrophobic material so as to retain said substrate therein, and a hydrophilic portion having a reporter moiety thereupon, said substrate being capable of being cleaved by said enzyme so as to produce a hydrophilic fragment which includes said reporter moiety.

14. The assay as in claim 13, wherein said body of hydrophobic material is disposed upon a support.

15. The assay as in claim 14, wherein said hydrophobic material is covalently attached to said support.

16. The assay as in claim 13, wherein said hydrophobic material is a lipid.

17. The assay as in claim 16, wherein said lipid comprises phosphatidylethanolamine.

18. The assay as in claim 13, wherein said reporter comprises a radioactive material or a non-radioactive material.

* * * * *